(12) United States Patent
Liu et al.

(10) Patent No.: US 8,943,872 B2
(45) Date of Patent: Feb. 3, 2015

(54) GAS CHROMATOGRAPHY—INVERSE GAS CHROMATOGRAPHY COMBINED ANALYSIS DEVICE

(75) Inventors: Baizhan Liu, Shanghai (CN); Wenjuan Wang, Shanghai (CN); Saijing Zheng, Shanghai (CN); Da Wu, Shanghai (CN)

(73) Assignee: Shanghai Tobacco Group Co., Ltd., Shanghai (CN)

( * ) Notice: Subject to any disclaimer, the term of this patent is extended or adjusted under 35 U.S.C. 154(b) by 114 days.

(21) Appl. No.: 13/809,586

(22) PCT Filed: Jul. 15, 2011

(86) PCT No.: PCT/CN2011/077205
§ 371 (c)(1),
(2), (4) Date: Apr. 10, 2013

(87) PCT Pub. No.: WO2012/139340
PCT Pub. Date: Oct. 18, 2012

(65) Prior Publication Data
US 2013/0192340 A1 Aug. 1, 2013

(30) Foreign Application Priority Data
Apr. 11, 2011 (CN) .......................... 2011 1 0089316

(51) Int. Cl.
*G01N 30/02* (2006.01)
*G01N 30/46* (2006.01)

(52) U.S. Cl.
CPC .............. *G01N 30/02* (2013.01); *G01N 30/461* (2013.01)
USPC ....................................................... 73/23.35

(58) Field of Classification Search
CPC G01N 2030/025; G01N 30/461; G01N 30/02

USPC ............................................... 73/23.35, 23.39
See application file for complete search history.

(56) References Cited

U.S. PATENT DOCUMENTS

| | | | | | |
|---|---|---|---|---|---|
| 4,962,042 | A | * | 10/1990 | Morabito et al. | 436/161 |
| 6,134,945 | A | * | 10/2000 | Gerstel et al. | 73/23.42 |
| 6,490,910 | B1 | * | 12/2002 | Butler et al. | 73/23.42 |
| 8,062,905 | B1 | * | 11/2011 | Meece | 436/181 |

* cited by examiner

*Primary Examiner* — Hezron E Williams
*Assistant Examiner* — David Z Huang
(74) *Attorney, Agent, or Firm* — Tianhua Gu; Global IP Services

(57) ABSTRACT

The present invention provides a gas chromatography—inverse gas chromatography combined analysis device, which includes a gas chromatography column and an inverse gas chromatography column, an input end of the gas chromatography column is connected to a sample feeder, an output end of the gas chromatography column is connected to an input end of the inverse gas chromatography column, the output end of the gas chromatography column is further connected to a first detector, the input end of the inverse gas chromatography column is further connected to a carrier gas tube, an output end of the inverse gas chromatography column is connected to a second detector, and the first detector and the second detector are both connected to a signal collector. The present invention not only can investigate adsorption performance of a tested solid adsorption material with respect to a single probe, but also can investigate adsorption performance of different solid adsorption materials with respect to different constituents in a combined probe at the same time, thereby improving the development efficiency of the inverse gas chromatography technologies.

6 Claims, 1 Drawing Sheet

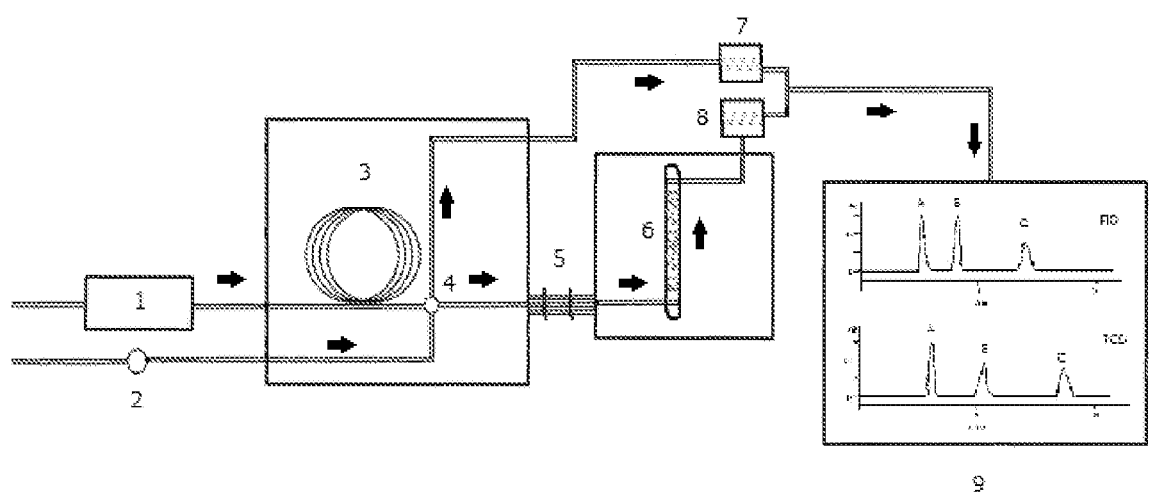

GAS CHROMATOGRAPHY—INVERSE GAS CHROMATOGRAPHY COMBINED ANALYSIS DEVICE

BACKGROUND OF THE PRESENT INVENTION

1. Field of Invention

The present invention relates to a device for testing surface properties of a solid material, and more particularly to a gas chromatography—inverse gas chromatography combined analysis device.

2. Description of Related Arts

In the past, in an evaluation process of surface performance of a solid material, technologies such as a scanning electron microscope and an X-ray energy spectrum are usually used to determine surface properties such as the specific surface area and the pore volume of an adsorbent. But the methods cannot reflect the capability of the interaction between a surface of a solid material and a probe interacting with the surface, and especially can hardly investigate the interaction between a solid material and different component substances of a combined probe. In conventional inverse gas chromatography, a solid material to be tested is packed into a packed column, and single-probe molecules to interact with the solid material to be tested are vaporized and then made to pass through the packed column. In this way, when probe molecules pass through a column packed with different kinds of materials, different relative retention times are incurred. According to a relative retention time value and other chromatographic parameters, the interaction between the probe molecules and the material surface under test can be investigated. However, when the conventional method is used to test some adsorption materials, a relative retention time during which probe molecules pass through the surface of the adsorption materials is not easy to be calculated. Especially for a combined probe, it is very difficult for the conventional inverse gas chromatography to distinguish them, which incurs the problem that constituents cannot be distinguished after peaks. Therefore, a standard sample is required during a test, which increases the difficulty of the test and is not conducive to the test of different constituents of a combined probe.

SUMMARY OF THE PRESENT INVENTION

The problem to be solved by the present invention is to provide a gas chromatography—inverse gas chromatography combined analysis device, so as to solve the problem in the prior art.

A gas chromatography—inverse gas chromatography combined analysis device according to the present invention comprises a gas chromatography column and an inverse gas chromatography column, an input end of the gas chromatography column is connected to a sample feeder, an output end of the gas chromatography column is connected to an input end of the inverse gas chromatography column, the output end of the gas chromatography column is further connected to a first detector, the input end of the inverse gas chromatography column is further connected to a carrier gas tube, an output end of the inverse gas chromatography column is connected to a second detector, and the first detector and the second detector are both connected to a signal collector.

In the present invention, the output end of the gas chromatography column and the input end of the inverse gas chromatography column are connected by a thermally insulated pipeline.

In the present invention, the gas chromatography column is a capillary column.

In the present invention, the inverse gas chromatography column is a packed column.

In the present invention, a flow regulating valve is disposed on the carrier gas tube.

In the present invention, the output end of the gas chromatography column, the first detector, the input end of the inverse gas chromatography column, and the carrier gas tube are connected by a four-way valve.

According to the technical solution, in the gas chromatography—inverse gas chromatography combined analysis device of the present invention, the principles of the inverse gas chromatography are used to measure the interaction between different probe molecules and a surface of a tested solid at a set temperature, such as surface adsorption enthalpy, surface acid-base properties, surface compatibility, a diffusion coefficient of probe molecules in an adsorbent, and various crystallization parameters, detect differences in surface chemical properties between different batches of samples, determine surface heterogeneity of a single-component or multi-component mixture (by measuring distribution of surface energy), and measure a glass transition temperature of a massive object. The device not only can investigate adsorption performance of a tested solid adsorption material with respect to a single probe, but also can investigate adsorption performance of different solid adsorption materials with respect to different constituents in a combined probe at the same time, so as to analyze the interaction force between the surface of a tested material and different probe molecules at the same time, thereby greatly improving the flexibility of the system and method, and improving and optimizing the conventional analysis method.

BRIEF DESCRIPTION OF THE DRAWINGS

FIG. 1 is a structural view of a gas chromatography—inverse gas chromatography combined analysis device according to the present invention.

List of Reference Numerals: 1 Sample feeder; 2 Flow regulating valve; 3 Gas chromatography column; 4 Four-way valve; 5 Thermally insulated pipeline; 6 Inverse gas chromatography column; 7 First detector; 8 Second detector; 9 Signal collector

DETAILED DESCRIPTION OF THE PREFERRED EMBODIMENTS

As shown in FIG. 1, a gas chromatography—inverse gas chromatography combined analysis device according to the present invention includes a gas chromatography column 3 and an inverse gas chromatography column 6. An input end of the gas chromatography column 3 is connected to a sample feeder 1. An output end of the gas chromatography column 3 is connected to an input end of the inverse gas chromatography column 6. The output end of the gas chromatography column 3 is further connected to a first detector 7. The input end of the inverse gas chromatography column 6 is further connected to a carrier gas tube. An output end of the inverse gas chromatography column 6 is connected to a second detector 8. The first detector 7 and the second detector 8 are both connected to a signal collector 9.

The output end of the gas chromatography column and the input end of the inverse gas chromatography column are connected by a thermally insulated pipeline 5, so as to ensure the temperature of a probe during operation.

The output end of the gas chromatography column 3, the first detector 7, the input end of the inverse gas chromatography column 6, and the carrier gas tube are connected by a four-way valve 4. A flow regulating valve 2 is disposed on the carrier gas tube, so as to regulate the input quantity of a carrier gas of the carrier gas tube. The first detector 7 and the second detector 8 may each be a thermal conductivity detector (TCD), or a hydrogen flame ionization detector (FID).

In the device, a gas may be directly fed, or a trace amount of liquid is fed. For example, headspace feeding is adopted, or liquid probe molecules to be tested are vaporized before being fed. The gas chromatography column 3 is a capillary column. The inverse gas chromatography column 6 is a packed column. The vaporized probe molecules first pass through a capillary column (a suitable capillary column may be selected according to actual needs) to have the temperature raised, and then are separated. After separation, the sample flowing out of the capillary column is divided, so that one part enters the first detector 7 to undergo detection, and the other part passes through the packed column and then enters the second detector 8 to undergo detection.

In the device, the input end of the inverse gas chromatography column 6 is further connected to the carrier gas tube, so that a part of carrier gas and the sample flowing out of the capillary column together pass through the packed column, so that when the flow of the carrier gas in the capillary column is limited, the flow of the carrier gas passing through the packed column is not affected. An additional carrier gas outside the capillary column passes through the packed column, so as to reduce the requirements on the inner diameter of the gas chromatography capillary column and reasonably design the flow of the carrier gas passing through the packed column, thereby making the test more scientific and flexible.

In the device, two detectors are used to perform the detection at the same time. Different peak times of the probe molecules on the two detectors are investigated, and therefore a relative retention time during which the probe molecules pass through a material in the packed column is determined, so as to test the interaction between different probe molecules and the material to be tested and surface properties of the material to be tested.

In the device, before the interaction between the combined probe and the surface of the material to be tested is tested, the combined probe is made to pass through the gas chromatography column, and is separated, so as to effectively avoid the problem that it is difficult for the peaks of the gas chromatography to be distinguished after the combined gas phase probe directly passes through the inverse gas chromatography column. Therefore, the problem that a conventional inverse gas chromatography system can only perform determination on a single-probe is alleviated significantly, thereby simplifying the operation. The device achieves the combination of the gas chromatography and the inverse gas chromatography, exerts the function of the gas chromatography in separating probe molecules to the greatest extent possible, makes the system and method more scientific and reasonable and the detection more convenient, and makes it possible to test the interaction between different constituents in a combined probe and the surface of a solid material at the same time, which greatly simplifies the test process of other surface properties of a solid material.

During the test, different constituents of combined-probe molecules are well separated through the gas chromatography column 3, which effectively avoids the problem that when a conventional inverse gas chromatography device performs test, it is difficult to distinguish peaks after a mixed gas phase probe directly passes through a column packed with a material with excellent adsorption performance. The surface properties are investigated according to different specific retention times during which the different constituents in the combined probe pass through the adsorption material to be tested, so as to compare the interaction between the same kind of probe molecules and the surface of different solid materials or the interaction between different kinds of probe molecules and the surface of the same solid material, and further determine other surface properties of the material under test through the test.

A specfic embodiment of the present invention is as follows. The sample feeder is a rotary disk auto sample feeder, which is an Agilent 6890N gas chromatograph. The model of the capillary column is CP-Poraplot-Q, and the capillary column has the length being 27.5 m and the inner diameter being 0.53 mm. The inverse gas chromatography column is a packed column, and the packed column has the inner diameter being 2 mm, the outer diameter being 6 mm, and the length being 8 cm. The column temperature is 200° C., the flow of the carrier gas is 26.5 mL/min, and the quantity of the fed sample is 0.2 μl. The split ratio at a sample feeding port is 30:1, the temperature at the sample feeding port is 250° C., the detectors are an FID detector and a TCD detector, and the temperatures are both 250° C. The following experiment is performed. The packed column is filled with 16 mg of a sample to be tested. Acetaldehyde, acetone, butyraldehyde, benzene, carbon tetrachloride, tetrahydrofuran, and ethyl acetate are used as probe molecules, so as to test the adsorption performance thereof on the surface of a solid adsorption material to be tested.

During the experiment, first the prepared packed column is mounted on a well adjusted gas chromatograph and the air tightness is ensured, and the flow of a carrier gas is regulated. A gas flow method is used to age an inverse gas chromatography column, that is, an input end of the inverse gas chromatography column is connected to an output A carrier gas (the flow rate being 10.5 mL/min) is input for half an hour, so as to remove air in the system. The temperature of the chromatographic column is raised, and is controlled to be about 200° C. for aging for 2 hours. After the aging, the detectors are connected for checking, so as to obtain stable baselines.

A calculation method of adsorption free energy ΔG of the solid material for the probe molecules is as follows.

$$\Delta G = -RT\ln Vg + K \quad (1)$$

In the formula, ΔG is standard adsorption free energy (J/mol); R is a universal gas constant being 8.3145 J/(mol·K); T is the absolute temperature (K); the value of K depends on the amount of polymer, the surface area, and an adsorption state, so that K is a constant (J/mol) in a same chromatographic column.

A specific retention volume Vg may be obtained through the following formula.

$$Vg = \Delta t * \frac{F}{m} * \frac{273.15}{T} * \frac{3}{2} * \frac{(Pi/Po)^2 - 1}{(Pi/Po)^3 - 1} \quad (2)$$

In the formula, $\Delta t = t_r - t_0$, $t_r$ and $t_0$ are a retention time (s) and a dead time (s) of probe molecules respectively; F is the flow rate (mL/s) of the carrier gas at the outlet of the inverse gas chromatography column; m is the mass (g) of a fixed phase; T is the ambient temperature (K); $P_i$ and $P_0$ are pressures (Pa) at the inlet and the outlet of the inverse gas chromatography column respectively; Vg is the specific retention volume (mL/g).

In embodiments 1 to 7, adsorption performance of a material A to be tested with respect to different probes is investigated, and results obtained according to the formulas (1) and (2) are as follows:

TABLE 1

Investigation of adsorption performance of a solid material A at 200° C. with respect to different gas phase probes

| Embodiments | Name of the tested sample | $\Delta G$, kJ/mol |
|---|---|---|
| 1 | Investigation of the adsorption free energy of the material A with respect to acetaldehyde | −19.4651 |
| 2 | Investigation of the adsorption free energy of the material A with respect to acetone | −24.9012 |
| 3 | Investigation of the adsorption free energy of the material A with respect to butyraldehyde | −28.8257 |
| 4 | Investigation of the adsorption free energy of the material A with respect to benzene | −38.489 |
| 5 | Investigation of the adsorption free energy of the material A with respect to ethyl acetate | −31.9238 |
| 6 | Investigation of the adsorption free energy of the material A with respect to tetrahydrofuran | −28.1969 |
| 7 | Investigation of the adsorption free energy of the material A with respect to carbon tetrachloride | −30.832 |

It can be seen from the results of the embodiments that the adsorption performance of the solid adsorption material A with respect to different gas phase probes is different, so that the method can evaluate adsorption performance of an adsorption material with respect to different probe molecules.

A calculation method of the adsorption enthalpy $\Delta H$ and entropy $\Delta S$ of the surface of the solid material A with respect to different probes is as follows.

According to a thermodynamic formula $\Delta G=\Delta H-T\Delta S$ and the formula (1), it can be obtained that:

$$-RT\ln Vg = \Delta H - T\Delta S \qquad (3)$$

therefore:

$$\Delta H = -R \times \frac{\partial(\ln Vg)}{\partial(1/T)}. \qquad (4)$$

In the formula, Vg is the specific retention volume (mL/g), R is the universal gas constant being 8.3145 J/(mol·K), and T is the ambient temperature (K).

Drawing is made on $\ln Vg$ versus $1/T$, and the adsorption enthalpy and the entropy value of the tested sample with respect to different probes may be obtained according to the slope of an obtained straight line and an intercept.

Embodiments 8 to 12 are detection of surface adsorption enthalpy of the solid material A with respect to different gas phase constituents such as acetone, ethanol, tetrahydrofuran, carbon tetrachloride, and ethyl acetate, and results obtained according to the formula (4) are as follows:

TABLE 2

Surface adsorption enthalpy of the solid material A with respect to different gas phase constituents

| Embodiments | Name of the tested sample | $\Delta H$, kJ/mol |
|---|---|---|
| 8 | Investigation of the surface adsorption enthalpy of the material A with respect to acetone | −47.055 |
| 9 | Investigation of the surface adsorption enthalpy of the material A with respect to ethanol carbon | −37.141 |
| 10 | Investigation of the surface adsorption enthalpy of the material A with respect to tetrahydrofuran | −53.081 |
| 11 | Investigation of the surface adsorption enthalpy of the material A with respect to carbon tetrachloride | −53.307 |
| 12 | Investigation of the surface adsorption enthalpy of the material A with respect to ethyl acetate | −62.666 |

According to the acid-base theory of Gutmann, in combination with the surface adsorption enthalpy $\Delta H$ of the material A with respect to the probe molecules that is measured through the above method, an acidity constant and an alkaline constant of the surface thereof may be calculated through the following method:

$$-\Delta H = K_a \times DN + K_b \times AN \qquad (5)$$

In the formula, DN and AN are defined by Gutmann and are respectively an electron donor constant and an electron acceptor constant of probe molecules, and Ka and Kb are an acidity constant and an alkaline constant of the surface of an adsorbent respectively. Drawing is made on $-\Delta H/AN$ versus $DN/AN$ for multiple kinds of polar probes, and a constant Ka and a constant Kb being semi-quantitative and indicating the acid-base properties of the surface of the adsorbent may be obtained from the slope of an obtained straight line and an intercept.

Embodiments 13 to 15 are test results of acid-base properties of the surface of the solid material A, and the results obtained according to the formula (5) are as follows.

TABLE 3

Test results of acid-base properties of the surface of the solid material A

| Embodiments | Name of the tested sample | |
|---|---|---|
| 13 | The acidity constant Ka of the surface of the material A | 2.3612 |
| 14 | The alkaline constant Kb of the surface of the material A | 1.2206 |
| 15 | Ka/Kb | 1.9344 |

It can be seen from the embodiments 13 to 15 that the ratio of the acidity constant to the alkaline constant of the material A is greater than 1, which indicates that the acidity is strong.

What is claimed is:

1. A gas chromatography—inverse gas chromatography combined analysis device, comprising a gas chromatography column and an inverse gas chromatography column, wherein an input end of the gas chromatography column is connected to a sample feeder, an output end of the gas chromatography column is connected to an input end of the inverse gas chromatography column, the output end of the gas chromatography column is further connected to a first detector, the input end of the inverse gas chromatography column is further connected to a carrier gas tube, an output end of the inverse gas chromatography column is connected to a second detector, and the first detector and the second detector are both connected to a signal collector.

2. The gas chromatography—inverse gas chromatography combined analysis device as in claim 1, wherein the output end of the gas chromatography column and the input end of the inverse gas chromatography column are connected by a thermally insulated pipeline.

3. The gas chromatography—inverse gas chromatography combined analysis device as in claim 1, wherein the gas chromatography column is a capillary column.

4. The gas chromatography—inverse gas chromatography combined analysis device as in claim 1, wherein the inverse gas chromatography column is a packed column.

5. The gas chromatography—inverse gas chromatography combined analysis device as in claim 1, wherein a flow regulating valve is disposed on the carrier gas tube.

6. The gas chromatography—inverse gas chromatography combined analysis device as in claim 1, wherein the output end of the gas chromatography column, the first detector, the input end of the inverse gas chromatography column, and the carrier gas tube are connected by a four-way valve.

\* \* \* \* \*